(12) United States Patent
Yoshitake et al.

(10) Patent No.: US 6,306,992 B1
(45) Date of Patent: Oct. 23, 2001

(54) CARBOSILOXANE DENDRIMER AND DENDRIMER-CONTAINING ORGANIC POLYMERS

(75) Inventors: Makoto Yoshitake; Tadashi Okawa; Yoshitsugu Morita; Haruhiko Furukawa, all of Chiba Prefecture (JP)

(73) Assignee: Dow Corning Toray Silicone Company, Ltd., Tokyo (JP)

( * ) Notice: Subject to any disclaimer, the term of this patent is extended or adjusted under 35 U.S.C. 154(b) by 0 days.

(21) Appl. No.: 09/625,011

(22) Filed: Jul. 25, 2000

(30) Foreign Application Priority Data

Jul. 30, 1999 (JP) .................................................. 11-216468

(51) Int. Cl.$^7$ .................................................. C08F 230/08
(52) U.S. Cl. .............................. 526/279; 528/15; 528/25; 528/31; 528/32
(58) Field of Search .............................. 526/279; 528/15, 528/25, 31, 32

(56) References Cited

FOREIGN PATENT DOCUMENTS

| | | | |
|---|---|---|---|
| 1-055674-A1 | * 11/2000 | (EP) . | |
| 01-254791 | 10/1989 | (JP) | ................................. C08F/293/00 |
| 01-319518 | 12/1989 | (JP) | ................................. C08F/290/06 |
| 07-196975 | 8/1995 | (JP) | ................................. C09D/133/08 |
| 11-001485 | 1/1999 | (JP) | ................................. C07F/7/08 |
| 11-001530 | 1/1999 | (JP) | ................................. C08F/299/08 |

* cited by examiner

Primary Examiner—Robert Dawson
Assistant Examiner—Marc S. Zimmer
(74) Attorney, Agent, or Firm—Alan Zombeck

(57) ABSTRACT

A novel carbosiloxane dendrimer is disclosed containing a radically polymerizable group in the molecule and which possesses excellent polymerization reactivity. The carbosiloxane dendrimer can be used to provide organic polymers as afforded by the polymerization of the carbosiloxane dendrimer either alone or with other organic monomers. The radically polymerizable group-functional carbosiloxane dendrimer with the general formula

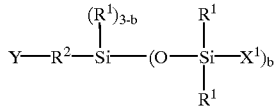

($R^1$ is $C_1$ to $C_{10}$ alkyl or aryl, $R^2$ is a divalent organic group excluding $C_1$ to $C_{10}$ alkylene, b is 1 to 3, $X^1$ is a silylalkyl group, and Y is a radically polymerizable group). Also, dendrimer-containing organic polymer as afforded by the polymerization of (A) the aforesaid carbosiloxane dendrimer and (B) radically polymerizable organic monomer.

4 Claims, No Drawings

CARBOSILOXANE DENDRIMER AND DENDRIMER-CONTAINING ORGANIC POLYMERS

FIELD OF THE INVENTION

This invention relates to a novel carbosiloxane dendrimer and to organic polymers containing this novel dendrimer. More particularly, this invention relates to a carbosiloxane dendrimer that contains a radically polymerizable group in each molecule and to the dendrimer-containing organic polymers afforded by the polymerization of this novel carbosiloxane dendrimer.

BACKGROUND OF THE INVENTION

Organopolysiloxanes that contain a radically polymerizable group (e.g., acryloxy or methacryloxy) in each molecule are known. Known in this regard are, for example, straight-chain polydimethylsiloxanes in which only a single terminal is endblocked by methacryloxypropyl and the following polydimethylsiloxane having a single branch point in the molecule

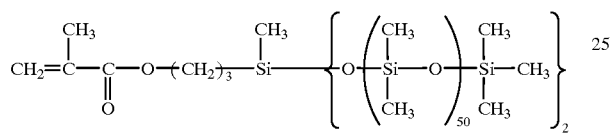

are described in Japanese Laid Open (Kokai or Unexamined) Patent Application Numbers Hei 7-196975 (196,975/1995), Hei 1-319518 (319,518/1989), and Hei 1-254719 (254,719/1989)). The use of these straight-chain organopolysiloxanes and branched organopolysiloxanes as co-monomers in the synthesis of various organic resins provides copolymers that have a low surface tension and an excellent surface lubricity. These copolymers, however, have poor compatiblilty with non-silicone-type organic resins.

In response to this problem, the present inventors have already disclosed a carbosiloxane dendrimer in the form of a multibranched siloxane-silalkylene copolymer that contains in each molecule one radically polymerizable group and at least 2 branch points (Japanese Laid Open (Kokai or Unexamined) Patent Application Numbers Hei 11-1485 (1,485/1999) and Hei 11-1530 (1,530/1999)). This carbosiloxane dendrimer can, for example, be reacted with other radically polymerizable monomers to produce a variety of graft copolymers bearing pendant dendrimer structures. However, the radically polymerizable group and the dendrimer structure in this dendrimer are either directly bonded to each other or are bonded to each other across a lower alkylene group such as the propylene group. As a consequence, when this dendrimer is polymerized by itself or at high concentrations with other organic monomers, the reactivity is lowered by steric hindrance and the reaction does not proceed to completion.

SUMMARY OF THE INVENTION

The object of the present invention is to provide a novel carbosiloxane dendrimer that contains a radically polymerizable group in the molecule and which exhibits excellent polymerization reactivity. Another object of this invention is to provide dendrimer-containing organic polymers as afforded by the polymerization of the novel carbosiloxane dendrimer described herein.

This invention provides a radically polymerizable group-functional carbosiloxane dendrimer having the general formula

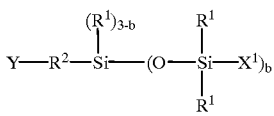

in which $R^1$ is a $C_1$ to $C_{10}$ alkyl group or aryl group; $R^2$ is a divalent organic group excluding $C_1$ to $C_{10}$ alkylene; b is 1 to 3; $X^1$ is the silylalkyl group with the following formula at i=1

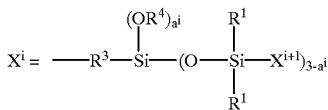

where $R^1$ is defined as above; $R^3$ is $C_2$ to $C_{10}$ alkylene; $R^4$ is $C_1$ to $C_{10}$ alkyl;

$X^{i+1}$ is selected from hydrogen, $C_1$ to $C_{10}$ alkyl and aryl, and the above-defined silylalkyl group; i is an integer with a value from 1 to 10 that specifies the generation of said silylalkyl group; and $a^i$ is from 0 to 3;

and Y is a radically polymerizable group selected from $C_2$ to $C_{10}$ alkenyl, groups with the following general formula in which $R^5$ is hydrogen or methyl

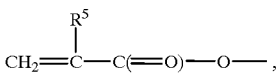

groups with the following general formula in which $R^5$ is hydrogen or methyl

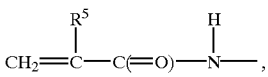

and groups with the following general formula

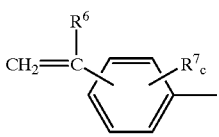

where $R^6$ is hydrogen or methyl, $R^7$ is $C_1$ to $C_{10}$ alkyl, and c is 0 to 4.

This invention additionally relates to dendrimer-containing organic polymer prepared by the polymerization of (A) 100 to 0.1 weight % of the above-described carbosiloxane dendrimer, and (B) 0 to 99.9 weight % of a radically polymerizable organic monomer.

DETAILED DESCRIPTION OF THE INVENTION

The carbosiloxane dendrimer of this invention is defined by the following general formula.

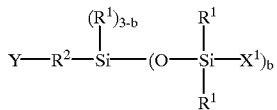

$R^1$ in this general formula denotes a $C_1$ to $C_{10}$ alkyl group or aryl group. The alkyl groups encompassed by $R^1$ can be exemplified by methyl, ethyl, propyl, butyl, pentyl, isopropyl, isobutyl, cyclopentyl, and cyclohexyl. The aryl groups encompassed by $R^1$ can be exemplified by phenyl and naphthyl. Methyl is preferred among the preceding for $R^1$. $R^2$ in the preceding general formula may be any group other than $C_1$ to $C_{10}$ alkylene, but is preferably a divalent organic group composed of a plural number of elements selected from carbon, silicon, hydrogen, oxygen, nitrogen, and sulfur. $R^2$ is even more preferably a divalent organic group that connects the Y and Si through at least 5 atoms. $R^2$ can be specifically exemplified by groups with the following structures.

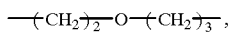

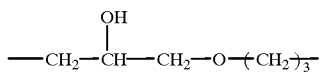

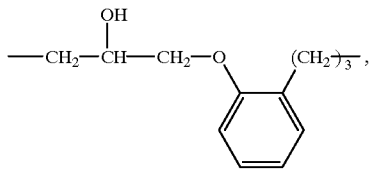

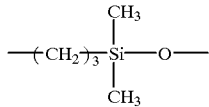

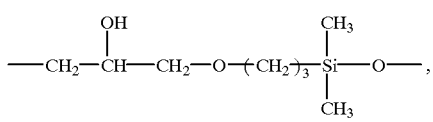

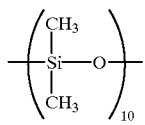

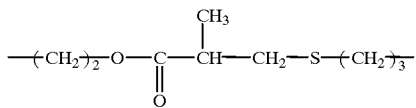

The group Y in the preceding general formula is a radically polymerizable group selected from;

$C_2$ to $C_{10}$ alkenyl, groups with the following general formula in which $R^5$ is hydrogen or methyl

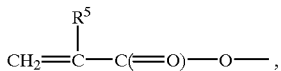

groups with the following general formula in which $R^5$ is hydrogen or methyl

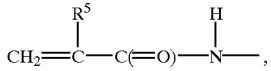

and or groups with the following general formula

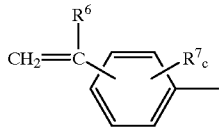

where $R^6$ is hydrogen or methyl, $R^7$ is $C_1$ to $C_{10}$ alkyl, and c is 0 to 4.

This radically polymerizable group Y can be specifically exemplified by acryloxy, methacryloxy, acrylamide, methacrylamide, 4-vinylphenyl, 3-vinylphenyl, 4-(2-propenyl)phenyl, 3-(2-propenyl)phenyl, 4-methyl-3-vinylphenyl, 2-octyl-4-vinylphenyl, vinyl, and 2-propenyl. The Y—$R^2$-moiety comprising Y bonded to the above-described $R^2$ can be exemplified by the following groups.

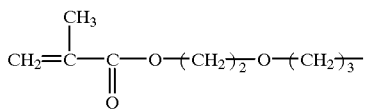

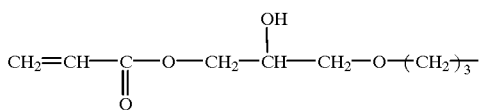

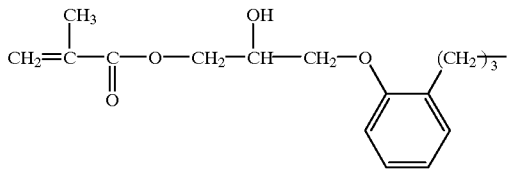

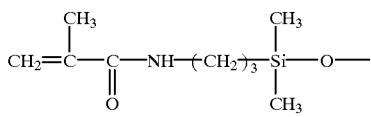

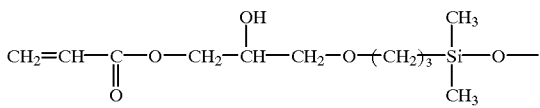

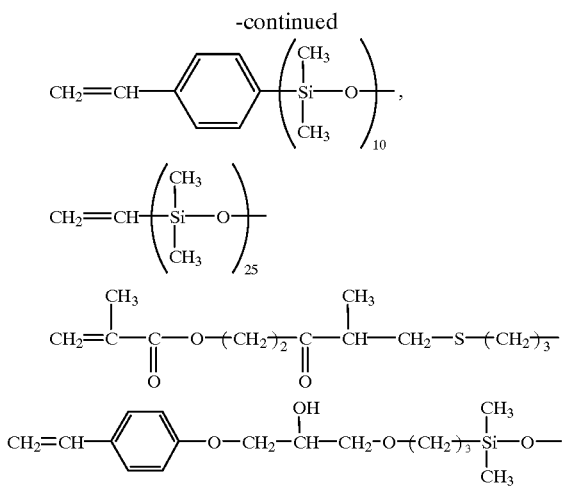

Preferred among the preceding are groups that contain an ether linkage, and groups that contain both an ether linkage and a siloxane bond, as shown below.

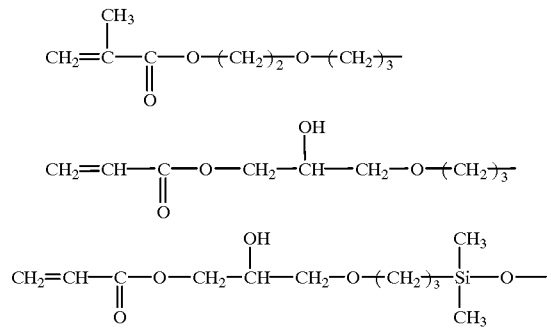

The subscript b in the preceding general formula has a value from 1 to 3 and is preferably 3. $X^1$ is the silylalkyl group with the following formula at i=1

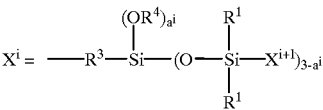

$R^1$ in the preceding formula for $X^i$ is defined as above, while $R^3$ is $C_2$ to $C_{10}$ alkylene, for example, straight-chain alkylene such as ethylene, propylene, butylene, and hexylene, or branched alkylene such as methylmethylene, methylethylene, 1-methylpentylene, and 1,4-dimethylbutylene. Preferred for $R^3$ among the preceding are ethylene, methylmethylene, hexylene, 1-methylpentylene, and 1,4-dimethylbutylene. $R^4$ is $C_1$ to $C_{10}$ alkyl, for example, methyl, ethyl, propyl, butyl, pentyl, isopropyl, isobutyl, cyclopentyl, and cyclohexyl. Methyl is preferred for $R^4$. $X^{i+1}$ in the preceding formula for $X^i$ is selected from hydrogen, a $C_1$ to $C_{10}$ alkyl, a $C_1$ to $C_{10}$ aryl, and the above-defined silylalkyl group. The subscript $a^i$ is from 0 to 3, and the average of the sum of $a^i$ in each molecule is preferably no more than $1.5^i \times 3$. i is an integer with a value from 1 to 10 that specifies the generation of said silylalkyl group, i.e., that indicates the number of repetitions of this silylalkyl group. Thus, the carbosiloxane dendrimer of the present invention has the following general formula when the number of generations is 1:

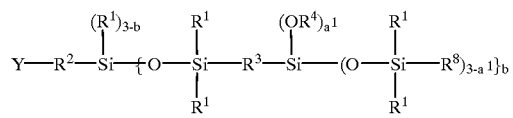

in the preceding formula, $R^1$, $R^2$, $R^3$, $R^4$, Y, and b are defined as above; $R^8$ is hydrogen or $R^1$; and $a^1$ is from 0 to 3. The inventive carbosiloxane dendrimer has the following general formula when the number of generations is 2:

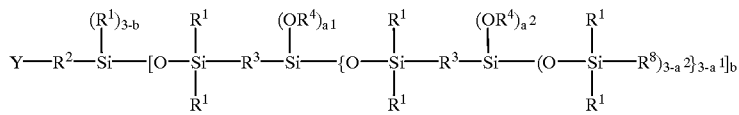

where $R^1$, $R^2$, $R^3$, $R^4$, $R^8$, Y, and b are defined as above and $a^1$ and $a^2$ are 0 to 3. The inventive carbosiloxane dendrimer has the following general formula when the number of generations is 3:

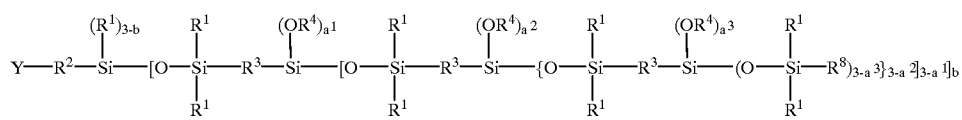

where in the preceding formula, $R^1$, $R^2$, $R^3$, $R^4$, $R^8$, Y, and b are defined as above and $a^1$, $a^2$, and $a^3$ are 0 to 3.

The inventive carbosiloxane dendrimer can be a single compound or a mixture of the subject compounds. The dispersity index for the molecular weight (polystyrene basis), that is, the weight-average molecular weight divided by the number-average molecular weight (Mw/Mn), is pref- erably no more than 2. The inventive carbosiloxane dendrimer can be specifically exemplified by polymers with the following average molecular formulas.

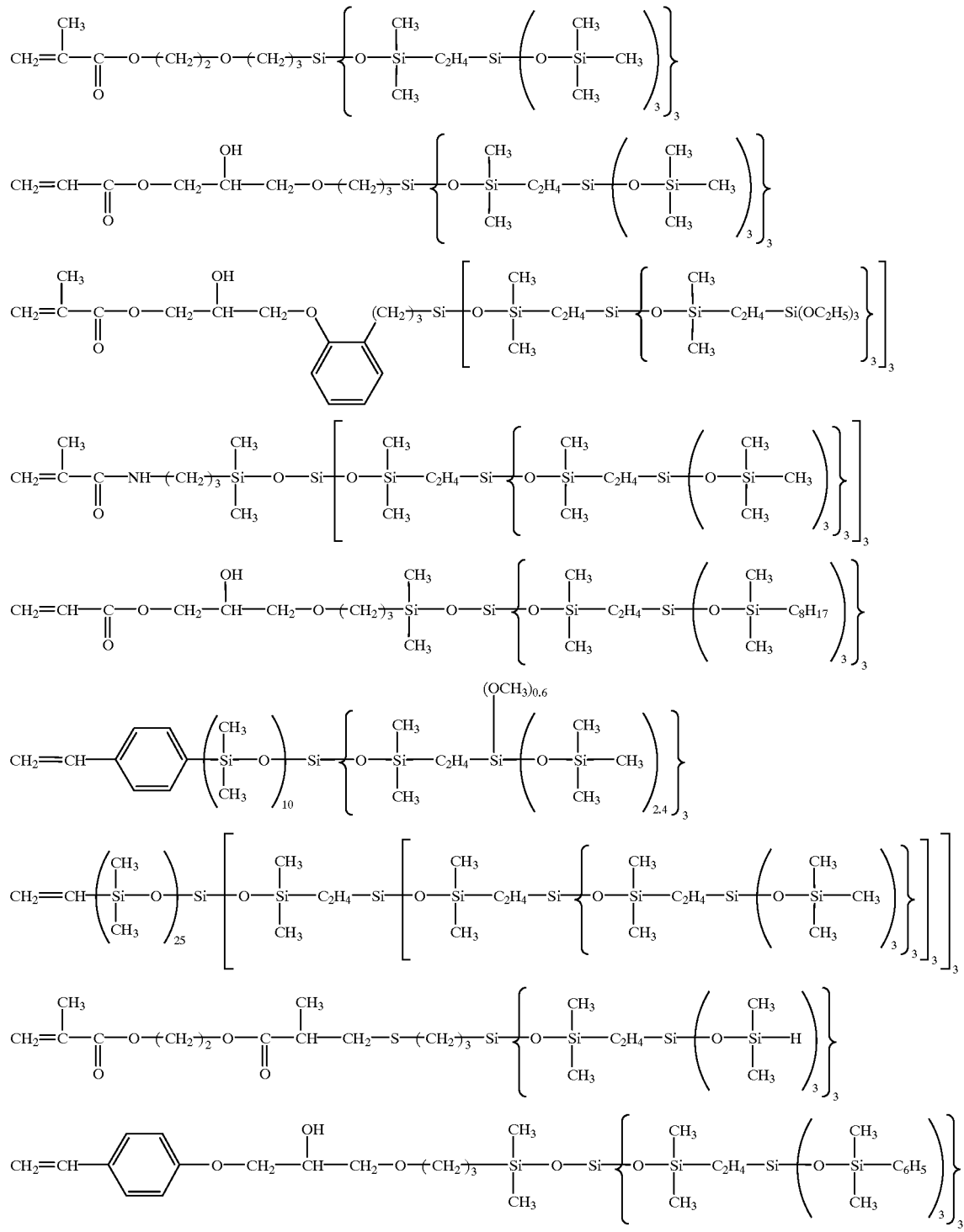

The inventive carbosiloxane dendrimer can be synthesized, for example, by suitable execututuion of the hereinbelow-described process (A), (B), (C), and (D), using the SiH-functional organosilicon compound with the following general formula as the initial starting reagent (referred to below simply as the starting reagent).

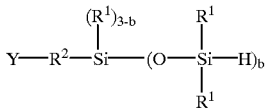

where Y, $R^1$, $R^2$, and b are defined as above.

(A) A process in which alkoxy-functional carbosiloxane dendrimer is synthesized by an addition reaction, in the presence of a platinum-type transition metal catalyst, between alkenyl-functional trialkoxysilane and the starting reagent or the SiH-functional carbosiloxane dendrimer prepared by process (B).

(B) A process in which the SiH-functional carbosiloxane dendrimer is obtained by reacting, under acidic conditions, the alkoxy-functional carbosiloxane dendrimer prepared by process (A) with disiloxane with the following general formula.

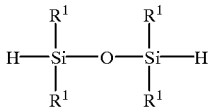

where $R^1$ is defined as above.

(C) A process in which carbosiloxane dendrimer is synthesized by an addition reaction, in the presence of a platinum-type transition metal catalyst, between alkenyl-functional organosiloxysilane with the general formula

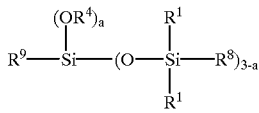

where $R^1$, $R^2$, and $R^8$ are defined as above; $R^9$ is $C_2$ to $C_{10}$ alkenyl; and a is a number from 0 to 3, and the starting reagent (see above) or the SiH-functional carbosiloxane dendrimer prepared by process (B).

(D) A process in which carbosiloxane dendrimer is synthesized by the addition reaction, in the presence of a platinum-type transition metal catalyst, between the SiH-functional carbosiloxane dendrimer afforded by process (B) and an alkenyl-functional hydrocarbon compound containing no more than 10 carbons, such as 1-butene, 1-hexene, and 1-octene.

The alkenyl-functional trialkoxysilane used in process (A) can be exemplified by vinyltrimethoxysilane, vinyltriethoxysilane, and hexenyltrimethoxysilane. The disiloxane used in process (B) can be exemplified by 1,1,3,3-tetramethyldisiloxane and 1,3-dimethyl-1,3-diphenyldisiloxane. The alkenyl-functional organosiloxysilane used in process (C) can be exemplified by vinyltris(trimethylsiloxy)silane and vinyltris (dimethylphenylsiloxy)silane. The platinum-type transition metal catalyst used in processes (A), (C), and (D) can be exemplified by chloroplatinic acid, alcohol-modified chloroplatinic acid, olefin complexes of platinum, and diketone complexes of platinum. The acid used to adjust process (B) into acidic conditions can be exemplified by hydrochloric acid, sulfuric acid, carboxylic acids, and sulfonic acids. The silicon-bonded hydrogen atom undergoes alcoholysis in process (B) with the production of small amounts of the monoalkoxysiloxy group with the following structure.

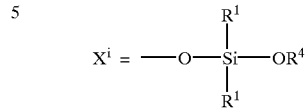

Where $R^1$ and $R^4$ are defined as above.

The carbosiloxane dendrimer of this invention can also be synthesized using the polymerizable group-free, SiH-functional organosilicon compound with the following general formula as the initial starting reagent

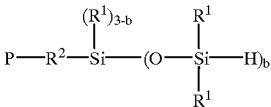

where $R^1$, $R^2$ and b are defined as above, while P is a halogen-, amino-, mercapto-, or epoxy-functional group. In this case, carbosiloxane dendrimer is first synthesized using the same processes as described above, and then, utilizing the reactivity of P, a radically polymerizable group is introduced in a final step by reaction with e.g., acrylic acid, methacrylic acid, acryloyl chloride, or methacryloyl chloride.

The dendrimer-containing organic polymers according to the present invention comprise the high-molecular-weight species afforded by polymerization of (A) 100 to 0.1 weight % inventive carbosiloxane dendrimer as described above and (B) 0 to 99.9 weight % radically polymerizable organic monomer.

The radically polymerizable organic monomer (B) must contain a radically polymerizable organic group, but is not particularly restricted otherwise. The radically polymerizable organic group is preferably vinyl, vinylene, or vinylidene. The radically polymerizable organic monomer encompassed by this component can be exemplified by the esters of unsaturated carboxylic acids, such as methyl acrylate, ethyl acrylate, propyl acrylate, n-butyl actylate, isobutyl acrylate, amyl acrylate, hexyl acrylate, 2-ethylhexyl acrylate, cyclohexyl acrylate, n-octyl acrylate, (glycidyl acrylate, 2-hydroxyethyl acrylate, 2-hydroxypropyl acrylate, 2,2,3,3-tetrafluoropropyl acrylate, octafluoropentyl acrylate, methyl methacrylate, ethyl methacrylate, n-butyl methacrylate, isobutyl methacrylate, 2-ethyhexyl methacrylate, lauryl methacrylate, tridecyl methacrylate, benzyl methacrylate, cyclohexyl methacrylate, tetrahydrofurfuryl methacrylate, 2-hydroxyethyl methacrylate, 2-hydroxypropyl methacrylate, glycidyl methacrylate, 2-methoxyethyl methacrylate, 2-ethoxyethyl methacrylate, and octafluoropentyl methaerylate; unsaturated aliphatic carboxylic acids such as methacrylic acid and acrylic acid; the amides of unsaturated aliphatic carboxylic acids, such as acrylamide, methacrylamide, and N-methylolacrylamide; unsaturated aliphatic nitriles, such as acrylonitrile and methacrylonitrile; unsaturated aliphatic compounds such as vinyl acetate, vinyl propionate, and vinyl versatate; unsaturated carboxylic acid anhydrides, such as maleic anhydride and 4-methacryloxyethyltrimellitic anhydride (4-META); vinyl halides such as vinyl chloride and vinyl fluoride; aromatic vinyl compounds such as styrene, methylstyrene, vinyltoluene and vinylpyridine; and aliphatic dienes such as butadiene and isoprene. The radically polymerizable organic monomer (B) can be a single monomer as described above or can be a mixture of two or more of such monomers. The indication of a 0 weight % participation by component (B) means that the organic polymers according to the present invention encompass the homopolymers of the carbosiloxane dendrimer (A).

The (A):(B) polymerization ratio, expressed as the weight ratio, should be in the range from 100:0 to 0.1 to 99.9 and is preferably in the range from 100:0 to 1:99.

The method for synthesizing the dendrimer-containing organic polymers of this invention is not critical. Radical polymerization and ionic polymerization methods can be used. The use of radical polymerization methods is preferred with solution polymerization techniques being particularly suitable therefor. This solution polymerization will typically be run by reacting 100 to 0.1 weight % (A) and 0 to 99.9 weight % (B) in a solvent for 3 to 20 hours at 50 to 150° C. in the presence of a radical initiator. Solvents usable for this reaction include, for example, aliphatic hydrocarbons such as hexane, octane, decane, and cyclohexane; aromatic hydrocarbons such as benzene, toluene, and xylene; ethers such as diethyl ether, dibutyl ether, tetrahydrofuran, and dioxane; ketones such as acetone, methyl ethyl ketone, methyl isobutyl ketone, and diisobutyl ketone; and esters such as methyl acetate, ethyl acetate, butyl acetate, and isobutyl acetate. Among the preceding, the use of toluene and xylene is particularly preferred. The radical initiator can in general be selected from those radical initiators heretofore known for use in radical polymerization methods, and can be specifically exemplified by azobis compounds such as 2,2'-azobis(isobutyronitrile), 2,2'-azobis(2-methylbutyronitrile), and 2,2'-azobis(2,4-dimethylvaleronitrile), and by organoperoxides such as benzoyl peroxide, lauroyl peroxide, tert-butyl peroxybenzoate, and tert-butyl peroxy-2-ethylhexanoate. A single radical initiator or a mixture of two or more radical initiators can be used. The radical initiator is preferably used at from 0.1 to 5 weight parts for each 100 weight parts of the sum of components (A) and (B). A chain transfer agent can also be used in the synthesis of the dendrimer-containing organic polymers of this invention. This chain transfer agent can be specifically exemplified by mercapto compounds such as 2-mercaptoethanol, butyl mercaptan, n-dodecyl mercaptan, and 3-mercaptopropyltrimethoxysilane, and by halogen compounds such as methylene chloride, chloroform, carbon tetrachloride, butyl bromide, and 3-chloropropyltrimethoxysilane.

Even when the carbosiloxane dendrimer of this invention as described hereinabove is polymerized by itself or at high concentrations, the reaction will proceed without the occurrence of gelation to give a high-molecular-weight dendrimer-containing orogenic polymer that exhibits an excellent transparency, water repellency, and gas permeability. Another advantage associated with inventive carbosiloxane dendrimer whose divalent organic group $R^2$ contains an ether linkage or an ether linkage+siloxane bond is that this type of carbosiloxane dendrimer enables the highly efficient introduction of the acryloxy group into the molecule. The introduction of the acryloxy group into such molecules has heretofore been problematic.

EXAMPLES

Example 1

96.8 g vinyltris(trimethylsiloxy)silane and 0.04 g 3% isopropanolic chloroplatinic acid solution were introduced into a 200-mL 4-neck flask fitted with a stirrer, thermometer, reflux condenser, and addition funnel, and the contents were heated to 100° C. while stirring. Then, 21.3 g 3-(2-methacryloxyethoxy)propyltris(dimethylsiloxy)silane was gradually added dropwise from the addition funnel so as to maintain a reaction temperature of 100 to 110° C. After the completion of this addition, the reaction solution was heated for an additional 1 hour at 120° C. The reaction solution was transferred after cooling to a pear-shaped flask and was concentrated under reduced pressure on a rotary evaporator to give 66.2 g of a colorless and transparent liquid. Analysis of this liquid by nuclear magnetic resonance analysis confirmed that the reaction product was a carbosiloxane dendrimer with the average molecular formula given below. According to gel permeation chromatography, this carbosiloxane dendrimer had a number-average molecular weight (polystyrene basis) of 1,163 and a dispersity of 1.02.

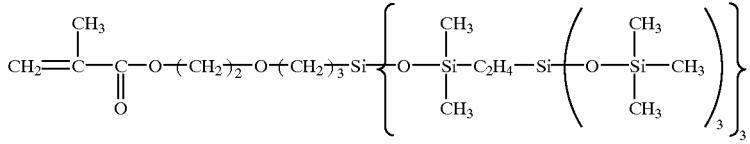

Example 2

11.7 g epoxy-functional carbosiloxane dendrimer with the formula

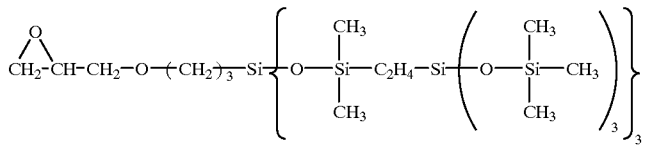

50 g toluene, and 0.25 g tetramethylguanidine were introduced into a 100-mL 4-neck flask fitted with a stirrer, thermometer, reflux condenser, and addition funnel, and the contents were heated to 90° C. while stirring. Then 1.44 g acrylic acid was added dropwise from the addition funnel over 30 minutes. After the completion of this addition, the reaction solution was heated for an additional 2 hours at 90°

C. The reaction solution was transferred after cooling to a pear-shaped flask and was concentrated under reduced pressure on a rotary evaporator to give 12.3 g of a transparent, yellowish brown liquid. Analysis of this liquid by nuclear magnetic resonance analysis confirmed that the reaction product was a carbosiloxane dendrimer with the average molecular formula given below. According to gel permeation chromatography, this carbosiloxane dendrimer had a number-average molecular weight (polystyrene basis) of 1,007 and a dispersity of 1.04.

was added to the solution remaining after distillation. The reaction was subsequently stirred for 2 hours while heating at 100° C. After then cooling to 60° C., 10 g methanol was added and stirring was continued for 1 hour at 60° C. After cooling, the reaction solution was transferred to a pear-shaped flask and was concentrated under reduced pressure on a rotary evaporator to give 48.5 g of a yellowish brown, transparent liquid. Analysis of this liquid confirmed the reaction product to be the carbosiloxane dendrimer with the average molecular formula given below. This product was designated intermediate A.

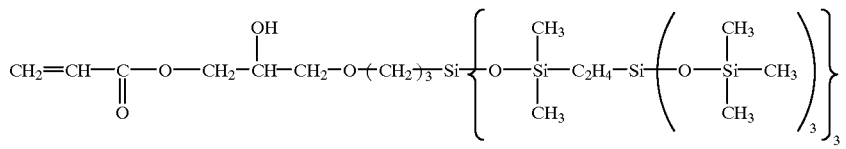

Example 3

13.1 g tetrakis(dimethylsiloxy)silane and 14 mg of a toluene solution (platinum concentration=2 weight %) of a platinum/divinyltetramethyldisiloxane complex were introduced into a 100-mL 4-neck flask fitted with a stirrer, thermometer, reflux condenser, and addition funnel, and the contents of the flask were heated to 100° C. while stirring. Then, 0.81 g N,N-bis(trimethylsilyl)allylamine was added dropwise from the addition funnel over a period of 10

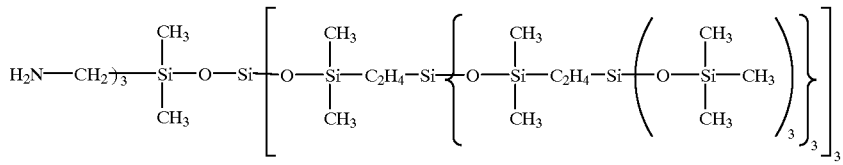

minutes. After the completion of addition, the reaction solution was heated for 2 hours at 90° C. After cooling, the reflux condenser was replaced with a distillation set up, and the flask was heated under reduced pressure and the unreacted tetrakis(dimethylsiloxy)silane was recovered by distillation. The distillation set up was then replaced with the reflux condenser, and, after cooling, 48.0 g vinyltris[dimethyl{tris(trimethylsiloxy)silylethyl}silyl]silane

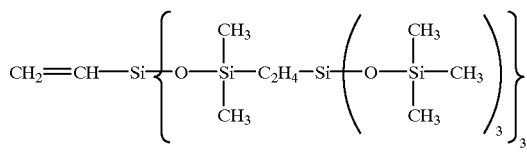

Next, 24.8 g intermediate A, 40 mg triethylamine, and 20 g toluene were introduced into a 100-mL 4-neck flask fitted with a stirrer, thermometer, reflux condenser, and addition funnel and the flask was stirred while being cooled on an ice water bath. Once cooled, 42 mg methacryloyl chloride was dripped in from a micro syringe. After the completion of this addition, the ice water bath was removed, and the suspended reaction solution was stirred for 2 hours at room temperature. The reaction solution was then transferred to a separatory funnel, diluted with 10 g, toluene, and washed 3 times with 50-mL, water. The resulting organic layer was dried over anhydrous sodium sulfate. After filtration, the filtrate was transferred to a pear-shaped flask and was concentrated under reduced pressure on a rotary evaporator to give 24.3 g of a yellowish brown, transparent liquid. Analysis of this liquid by nuclear magnetic resonance analysis confirmed this reaction product to be the carbosiloxane dendrimer with the average molecular formula given below. According to gel permeation chromatography, this carbosiloxane dendrimer had a number-average molecular weight (polystyrene basis) of 8,960 and a dispersity of 1.06.

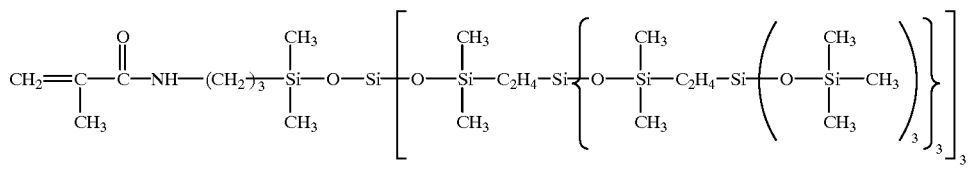

Example 4

19.8 g ethylene glycol dimethacrylate and 30 g toluene were introduced into a 100-mL three-neck flask fitted with a stirrer, thermometer, reflux condenser, and addition funnel and were heated to 50° C. while stirring. A liquid mixture of 12 g toluene, 0.40 g azobisisobutyronitrile, and 22.2 g 3-mercaptopropyltris[dimethyl{tris(dimethylsiloxy)} silylethylsiloxy]silane was then gradually added dropwise from the addition funnel. The reaction was continued for 2 hours after the completion of this addition. The reaction solution was subsequently transferred to a pear-shaped flask and concentrated on a rotary evaporator under a high vacuum to give 27.4 g of a yellowish brown, transparent liquid. Analysis of this liquid by nuclear magnetic resonance analysis confirmed the reaction product to be the carbosiloxane dendrimer with the average molecular formula given below. According to gel permeation chromatography, this carbosiloxane dendrimer had a number-average molecular weight (polystyrene basis) of 1,270 and a dispersity of 1.09.

A toluene solution was prepared by dissolving 2 g of this dendrimer-containing organic polymer in 18 g toluene. This solution was coated on the surface of a glass plate by spin coating. Air drying gave a film that had a contact angle versus water of 115°. For comparison, glass plate was similarly treated with polymethyl methacrylate and with poly(trimethylsiloxypropyl methacrylate). The polymethyl methacrylate film gave a contact angle versus water of 73°, while the poly(trimethylsiloxypropyl methacrylate) film gave a contact angle versus water of 100°.

Comparative Example 1

80 g toluene and 20 g methacryloxypropyl-functional carbosiloxane dendrimer with the following formula

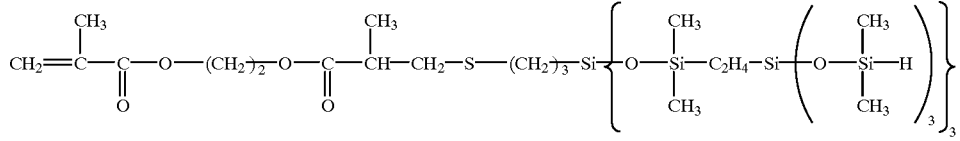

Example 5

20 g of the carbosiloxane dendrimer

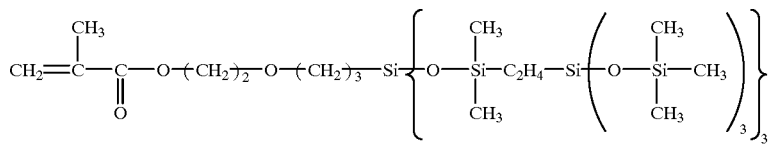

synthesized in Example 1 and 80 g toluene were introduced into a 100-mL four-neck flask fitted with a stirrer, thermometer, reflux condenser, and addition funnel and were heated to 70° C. under a nitrogen atmosphere while stirring. After reaction for 12 hours, the reaction solution was transferred to a pear-shaped flask and was concentrated under reduced pressure on a rotary evaporator to give 19.8 g of a colorless and transparent solid. Analysis of this solid by gel permeation chromatography confirmed the reaction product to be a high-molecular-weight dendrimer-containing organic polymer with a weight-average molecular weight (polystyrene basis) of 35,700.

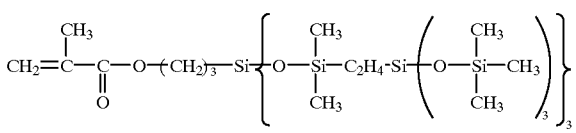

were introduced into a 100-mL four-neck flask fitted with a stirrer, thermometer, reflux condenser, and addition funnel and were heated to 70° C. under a nitrogen atmosphere while stirring. After reaction for 12 hours, the reaction solution was transferred to a pear-shaped flask and was concentrated under reduced pressure on a rotary evaporator to give 20.0 g of a colorless and transparent liquid. Analysis of this liquid by gel permeation chromatography confirmed that about 10% was low-molecular-weight material with a number-average molecular weight (polystyrene basis) no greater than 5,000 and about 90% was residual starting carbosiloxane dendrimer. These results confirmed that carbosiloxane dendrimer in which the radically polymerizable group is bonded to silicon across lower alkylene (e.g., propylene) has a diminished polymerization reactivity and is unable to produce high-molecular-weight homopolymer.

The carbosiloxane dendrimer of this invention is a novel and highly polymerizable compound that contains 1 radically polymerizable group in each molecule. The inventive carbosiloxane dendrimer enables the highly efficient synthesis of high-molecular-weight dendrimer-containing organic polymer that exhibits an excellent transparency, water repellency, and gas permeability.

What is claimed is:

1. A radically polymerizable group-functional carbosiloxane dendrimer having the general formula

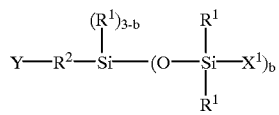

where $R^1$ is $C_1$ to $C_{10}$ alkyl or aryl; $R^2$ is a divalent organic group excluding $C_1$ to $C_{10}$ alkylene; b is 1 to 3; $X^1$ is the silylalkyl group with the following formula at i=1

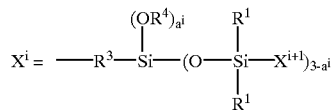

where $R^1$ is defined as above; $R^3$ is $C_2$ to $C_{10}$ alkylene; $R^4$ is $C_1$ to $C_{10}$ alkyl;

$X^{i+1}$ is selected hydrogen, $C_1$ to $C_{10}$ alkyl and aryl, and the above-defined silylalkyl group; i is an integer with a value from 1 to 10 that specifies the generation of said silylalkyl group; and $a^i$ is from 0 to 3;

and Y is a radically polymerizable group selected from $C_2$ to $C_{10}$ alkenyl, groups with the following general formula in which $R^5$ is hydrogen or methyl

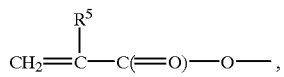

groups with the following formula in which $R^5$ is hydrogen or methyl

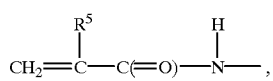

and groups with the following formula

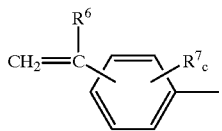

where $R^6$ is hydrogen or methyl, $R^7$ is $C_1$ to $C_{10}$ alkyl, and c is 0 to 4)}.

2. The carbosiloxane dendrimer of claim 1, in which $R^2$ is selected from

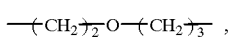

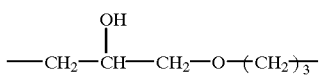

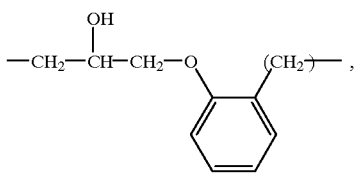

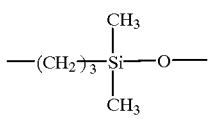

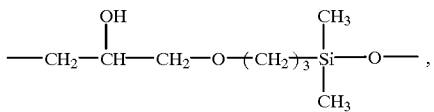

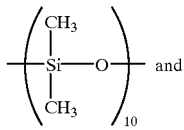 and

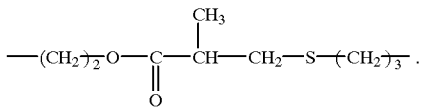

3. The carbosiloxane dendrimer of claim 1 having a formula selected from
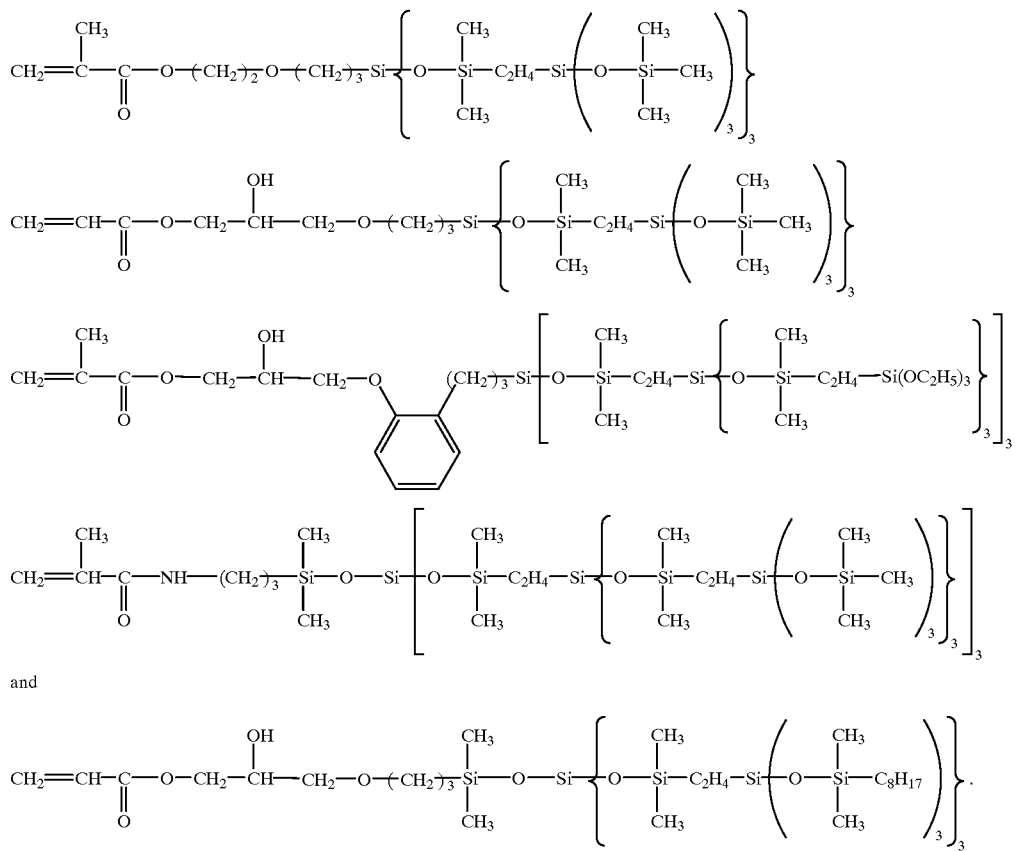
and
4. A dendrimer-containing organic polymer comprising the reaction product of the the polymerization of
  (A) 100 to 0.1 weight % of the radically polymerizable group-functional carbosiloxane dendrimer of claim 1 and
  (B) 0 to 99.9 weight % of a radically polymerizable organic monomer.
* * * * *